United States Patent [19]

Moore et al.

[11] 4,392,973
[45] Jul. 12, 1983

[54] METHOD FOR TRANSMITTING POWER BY TRACTION UTILIZING BORATE ESTERS AS TRACTION FLUIDS AND A DEVICE FOR USING THE METHOD

[75] Inventors: Anthony J. Moore, Camberley; Howard B. Silver, Esher, both of England

[73] Assignee: The British Petroleum Company Limited, London, England

[21] Appl. No.: 245,013

[22] Filed: Mar. 18, 1981

[30] Foreign Application Priority Data

Mar. 18, 1980 [GB] United Kingdom ............... 8009018

[51] Int. Cl.$^3$ .................... C09K 5/00; C10M 3/20
[52] U.S. Cl. ........................ 252/78.1; 252/49.6; 252/73; 252/75
[58] Field of Search ............ 252/49.6, 52 R, 73, 252/74, 75, 78.1; 74/200, 190; 568/1, 6

[56] References Cited

U.S. PATENT DOCUMENTS

| | | | |
|---|---|---|---|
| 2,795,548 | 6/1957 | Thomas et al. | 252/49.6 |
| 3,125,527 | 3/1964 | Krug et al. | 252/46.3 |
| 3,125,528 | 3/1964 | Kay et al. | 252/49.6 |
| 3,347,793 | 10/1967 | Washburn et al. | 252/49.6 |
| 3,356,707 | 12/1967 | Hinkamp et al. | 252/49.6 X |
| 3,440,894 | 4/1969 | Hammann et al. | 74/400 |
| 3,648,531 | 3/1972 | Duling et al. | 74/400 |
| 3,975,278 | 8/1976 | Wygant. | |
| 4,046,703 | 9/1977 | Duling et al. | 252/49 |

FOREIGN PATENT DOCUMENTS

| | | |
|---|---|---|
| 1287444 | 8/1972 | United Kingdom . |
| 1474048 | 5/1977 | United Kingdom . |
| 388012 | 10/1973 | U.S.S.R. . |

*Primary Examiner*—P. E. Willis, Jr.
*Attorney, Agent, or Firm*—Morgan, Finnegan, Pine, Foley and Lee

[57] ABSTRACT

A method for transmitting power by traction wherein the traction fluid is a borate ester having the general formula:

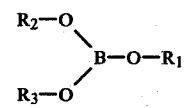

where $R_1$ is a saturated or unsaturated mono-cyclic group with from 1 to 5 side groups having from 1 to 20 carbon atoms, and $R_2$ and $R_3$ are the same or different cyclic groups as defined for $R_1$ or alkyl groups with from 1 to 20 carbon atoms.

A traction drive mechanism utilizing such a borate ester as the traction fluid.

6 Claims, No Drawings

METHOD FOR TRANSMITTING POWER BY TRACTION UTILIZING BORATE ESTERS AS TRACTION FLUIDS AND A DEVICE FOR USING THE METHOD

This invention relates to a method for transmitting power by traction in which borate esters are used as traction fluids.

Traction fluids are used as lubricants for drive mechanisms in which the drive is transmitted through the nominal point or line contact of rollers or cones and, for example, in continuously variable transmissions. Such transmissions are used on certain aircraft and are of current development interest in road vehicles because of their potential role in making more economic use of fuel.

The traction fluids used in such transmissions are required to transmit the torque between the rolling parts with a minimum of slippage, and must therefore have a high viscosity under the conditions of high shear and high pressure existing in the nip of the trasmission rollers. The performance of a traction fluid is usually assessed on the basis of its coefficient of traction, which is defined as the ratio of the tractive force to the normal load.

Naphthenic hydrocarbons are known to have good viscosity characteristics at high pressure and are often used as a major constituent of conventional traction fluids. However, such fluids become significantly less effective as the operating temperature rises.

According to the present invention a method of transmitting power by traction in which a traction fluid transmits the torque between rolling elements of a drive mechanism is characterised in that the traction fluid comprises a borate ester having the general formula:

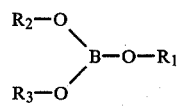

where $R_1$ is a saturated or unsaturated mono-cyclic group with from 1 to 5 side groups having from 1 to 20 carbon atoms, and $R_2$ and $R_3$ are the same or different cyclic groups as defined from $R_1$ or alkyl groups with from 1 to 20 carbon atoms.

If either $R_2$ or $R_3$ is an alkyl group it may be a primary, secondary or tertiary alkyl group.

$R_2$ and $R_3$ may be chemically joined to give a heterocyclic boron compound. $R_2$ and $R_3$ may be alkyl groups which are chemically joined for example, hexylene glycol alkyl borate or $R_2$ and $R_3$ may be cyclic groups with from 1 to 5 side groups which cyclic groups are chemically joined through side groups.

The preferred structure contains at least one and more preferably at least two saturated cyclic groups of six carbon atoms. For example, a suitable borate ester has the formula:

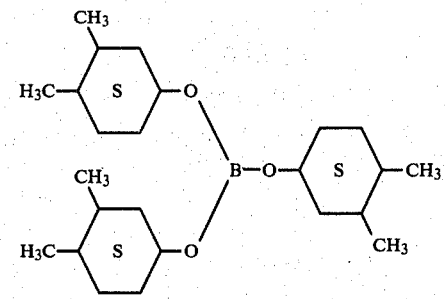

Tricycloalkyl or triaryl borates for use in the present invention, in which $R_1$, $R_2$ and $R_3$ are the same, may be prepared by standard methods involving the reaction of the appropriate hydroxy compound (alochol or phenol) with boric acid or boron trichloride. Mixed borates in which not more than two of $R_1$, $R_2$ and $R_3$ are the same may be prepared from borate esters, boron trihalides or boron hydrides. Suitably they may be prepared by transesterification.

An advantage of the borate esters over conventional traction fluids is that the trivalency of the boron allows groups to be incorporated into the molecules which may modify the physical or chemical properties of the fluids other than their tractant properties. Suitably, a sterically hindered borate ester may be used which is hydrolytically stable. A suitable ester has the formula:

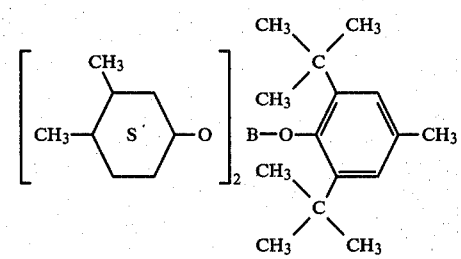

The borate esters according to the present invention have been found to have good traction coefficients and some have been found to have traction coefficients higher than those of known commercial traction fluids, particularly at temperatures higher than 100° C. Operation of traction drives at these relatively high temperatures is likely to become necessary in road vehicle applications as space and weight considerations are balanced against the provision of associated cooling systems.

The borate esters for use in the present invention preferably have a traction coefficient at 30° C. of at least 0.07 and more preferably of at least 0.10. The difference between the traction coefficients at 30° C. and 120° C. is preferably not more than 0.03 and is more preferably less than 0.01.

Conventional lubricant additives, e.g. anti-oxidants and viscosity index improvers may be present in the traction fluids for use in the present invention as necessary.

The traction fluids for use in the present invention may be single borate esters, mixtures of such esters or mixtures of the borate esters with other traction fluids.

The present invention includes a traction drive mechanism in which the torque between the rolling elements of the drive mechanism is transmitted by a traction fluid which is a borate ester as described above.

The invention is illustrated by the following examples.

EXAMPLE 1

Tri(3,4-dimethylcyclohexyl) borate

Tri(3,4-dimethylcyclohexyl) borate was prepared by the reaction of boric acid with 3,4-dimethylcyclohexanol as described in, for example, "Organoboron Chemistry" Vol. 1, by H Steinberg, (1964), Interscience Publishers, Chichester, and was isolated by distillation. The purity of the product was confirmed by infra-red spectroscopy and chemical analysis.

EXAMPLE 2

Bis(3,4-dimethylcyclohexyl) 2,6-di-t-butyl-4-methylphenyl borate

Bis(3,4-dimethylcyclohexyl) 2,6-di-t-butyl-4-methylphenyl borate was prepared by transesterification of tri(3,4-dimethylcyclohexyl) borate (1.5 mole) with 2,6-di-t-butyl-4-methylphenol (0.5 mole). The reaction mixture was slowly distilled to remove 3,4-dimethylcyclohexanol and the product was obtained as a viscous oil.

EXAMPLE 3 n-butyl 3,4-dimethylcyclohexyl 2,6-di-t-butyl-4-methylphenyl borate n-butyl 3,4-dimethylcyclohexyl 2,6-di-t-butyl-4-methylphenyl borate was prepared by successively transesterifying tri-n-butyl borate with 2,6-di-t-butyl-4-methylphenol and 3,4-dimethylcyclohexanol. Tri-n-butyl borate (1 mole) and 2,6-di-t-butyl-4-methylphenol (1 mole) were heated, with stirring, to a temperature of 280° C. and n-butanol collected as a distillate. After seven hours 0.81 moles had been collected and a total of 0.82 moles collected after ten hours. After cooling the reaction vessel and adding 1 mole of 3,4-dimethylcyclohexanol, the reaction mixture was again heated to 280° C. for six hours, after which time a further 0.9 moles of n-butanol had been collected. Volatile components were then removed under reduced pressure (90° C./0.1 mm) to leave a viscous golden yellow liquid as product.

EXAMPLE 4

Di-n-butyl 2,6-di-t-butyl-4-methylphenyl borate

Di-n-butyl 2,6-di-t-butyl-4-methylphenyl borate was prepared by reacting boric acid with n-butanol to give tri-n-butyl borate which was isolated by distillation. 2,6-di-t-butyl-4-methylphenol (1 mole) was added to the tri-n-butyl borate (1 mole). The reaction mixture was heated and n-butanol collected as distillate. The di-n-butyl 2,6-di-t-butyl-4-methylphenyl borate was isolated by distillation and its purity was confirmed by infra-red spectrascopy and chemical analysis.

The maximum traction coefficient of each of the fluids prepared in Examples 1 to 4 was measured using a rolling contact disc machine similar in principle to that described by W Hirst and A J Moore in Proc. Roy. Soc. Lond. A360 (1978) at pages 403–425.

The disc machine comprised two 152.4 mm diameter steel discs, hardened to 750 VPN, which were loaded against each other by a normal force W and rotated at independently controllable speeds of $U_1$ and $U_2$. The mean peripheral speed $\frac{1}{2}(U_1+U_2)$ is referred to as the rolling speed and the difference in speed $U_1+U_2$ as the slip. The discs had a surface finish of 0.015 μm centre line average. One disc was cylindrical and the other was crowned with a 229 mm radius. The discs had internal heating elements so that their surface temperature could be varied.

It is known that in an apparatus of this type rotation of the discs generates an elastohydrodynamic oil film at the point of contact, while the slip between them gives rise to a tangential (tractive) force, T. As the slip increases, the traction rises to a maximum value, $T_{max}$, and then falls. Thus, $T_{max}$ defines the limit of the torque that can be transmitted by the roller system.

The tractive capabilities of the fluids prepared in Examples 1 to 4 were compared with a commercially available traction fluid. Table I gives the values of their maximum traction coefficients, $T_{max}/W$, obtained at a load corresponding to a peak Hertz pressure of 1.45 GPa (210,000 lbf/in$^2$), a constant rolling speed of 2.4 m/s, and at roller surface temperatures varying from 30° C. to 150° C. The commercial tractant is a cycloaliphatic hydrocarbon and fluids A to D in Table I are as follows:

Fluid A is tri(3,4-dimethylcyclohexyl) borate as prepared in Example 1.

Fluid B is bis(3,4-dimethylcyclohexyl) 2,6-di-t-butyl-4-methylphenyl borate as prepared in Example 2.

Fluid C is n-butyl-3,4 dimethylcyclohexyl 2,6-di-t-butyl-4-methylphenyl borate as prepared in Example 3.

Fluid D is di-n-butyl 2,6-di-t-butyl-4 methylphenyl borate as prepared in Example 4.

The results show Fluids A and B to be inferior to the commercial tractant at the lower temperatures but markedly better at the higher temperatures of practical interest. Fluids C and D have lower values of maximum traction coefficient, at all temperatures, than the other three fluids. However, like Fluids A and B they each exhibit a relatively low rate of change of maximum traction coefficient with temperature and therefore retain a useful level of performance at high temperatures.

TABLE I

| LUBRICANT | DISC TEMPERATURE/°C. | | | | |
|---|---|---|---|---|---|
|  | 30 | 60 | 90 | 120 | 150 |
| Commercial Tractant | 0.117 | 1.106 | 0.088 | 0.078 | 0.072 |
| Fluid A | 0.106 | 0.108 | 0.101 | 0.098 | 0.088 |
| Fluid B | — | 0.098 | 0.100 | 0.095 | 0.095 |
| Fluid C | 0.078 | 0.076 | 0.071 | 0.069 | 0.065 |
| Fluid D | 0.074 | 0.070 | 0.066 | 0.060 | 0.055 |

We claim:

1. A method of transmitting power by traction wherein a traction fluid transmits the torque between rolling elements of a drive mechanism, comprises introducing between rolling elements of a drive mechanism a traction fluid consisting essentially of a borate ester having the general formula:

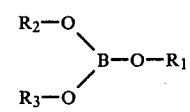

where $R_1$ is a saturated or unsaturated mono-cyclic hydrocarbyl group which from 1 to 5 side groups having from 1 to 20 carbon atoms, and $R_2$ and $R_3$ are the same or different cyclic hydrocarbyl groups as defined for $R_1$ or alkyl groups with from 1 to 20 carbon atoms.

2. A method of transmitting power by traction as claimed in claim 1 in which at least $R_1$ and $R_2$ are saturated cyclic hydrocarbyl groups with from 2 to 5 alkyl side groups each of which side groups has from 1 to 5 carbon atoms.

3. A method of transmitting power by traction as claimed in claim 2 in which $R_3$ is also a saturated cyclic hydrocarbyl group with from 2 to 5 alkyl side groups each of which side groups has from 1 to 5 carbon atoms.

4. A method of transmitting power by traction as claimed in claim 2 in which $R_3$ is an unsaturated cyclic hydrocarbyl group with from 2 to 5 alkyl side groups each of which side groups has from 1 to 5 carbon atoms.

5. A method of transmitting power by traction as claimed in claim 1 in which one of $R_1$, $R_2$ or $R_3$ is a sterically hindered cyclic hydrocarbyl group.

6. A traction drive mechanism in which the drive is transmitted by the method as claimed in claim 1.

* * * * *